(12) United States Patent
Yu (10) Patent No.: US 7,763,008 B2
(45) Date of Patent: Jul. 27, 2010

(54) METHOD EMPLOYING A DRAINAGE CATHETER ASSEMBLY FOR DELIVERING A CATHETER TO A BODY

(76) Inventor: Chun Ho Yu, Flat F, 21st Floor Tower 1, The Belcher's, 89 Pokfulam Road, Hong Kong (HK)

( * ) Notice: Subject to any disclaimer, the term of this patent is extended or adjusted under 35 U.S.C. 154(b) by 0 days.

(21) Appl. No.: 12/558,439

(22) Filed: Sep. 11, 2009

(65) Prior Publication Data
US 2010/0004622 A1 Jan. 7, 2010

Related U.S. Application Data

(62) Division of application No. 11/282,350, filed on Nov. 17, 2005, now Pat. No. 7,625,355.

(51) Int. Cl.
*A61M 1/00* (2006.01)
(52) U.S. Cl. ............... 604/506; 604/164.11; 604/541
(58) Field of Classification Search ........... 604/164.01, 604/164.06, 164.11, 164.13, 506, 507, 508, 604/540, 541
See application file for complete search history.

(56) References Cited

U.S. PATENT DOCUMENTS

| 3,406,685 A | 10/1968 | May |
| 3,993,079 A | 11/1976 | Henriques De Gatztanodo |
| 4,824,433 A | 4/1989 | März et al. |
| 4,986,814 A | 1/1991 | Burney et al. |
| 5,183,470 A | 2/1993 | Wettermann |
| 5,205,830 A | 4/1993 | Dassa et al. |
| 5,250,036 A | 10/1993 | Farivar |
| 6,264,624 B1 | 7/2001 | Desmond, III et al. |
| 6,562,024 B2 | 5/2003 | Alvarez de Toledo et al. |
| 6,641,564 B1 | 11/2003 | Kraus |
| 7,625,355 B2 * | 12/2009 | Yu .................. 604/164.01 |
| 2004/0193114 A1 | 9/2004 | Elbert et al. |
| 2005/0004523 A1 | 1/2005 | Osborne et al. |
| 2010/0049171 A1 * | 2/2010 | McQueen et al. ........ 604/540 |

FOREIGN PATENT DOCUMENTS

| CN | 2277243 Y | 4/1998 |
| CN | 2522037 Y | 11/2002 |
| CN | 1672649 A | 9/2005 |
| EP | 1457158 A2 | 9/2004 |
| WO | 03022337 A1 | 3/2003 |

* cited by examiner

*Primary Examiner*—Nicholas D Lucchesi
*Assistant Examiner*—Aarti B Berdichevsky
(74) *Attorney, Agent, or Firm*—The Maxham Firm

(57) ABSTRACT

A method for employing a pre-assembled drainage catheter assembly for the insertion of a drainage catheter percutaneously. The assembly includes a trocar, a cannula, a catheter stiffener, and a catheter. The drainage catheter assembly is operated between a pre-assembled condition, a first step condition and a second step condition. In the first step insertion the trocar and cannula are inserted into a patient's body for obtaining a specimen fluid before the catheter is inserted. In the second step the catheter is inserted for collecting fluid.

8 Claims, 7 Drawing Sheets

METHOD EMPLOYING A DRAINAGE CATHETER ASSEMBLY FOR DELIVERING A CATHETER TO A BODY

BACKGROUND OF THE INVENTION

1. Field of the Invention

The present invention relates to catheters, and more particularly to a catheter assembly which facilitates the percutaneous drainage of abnormal fluid collections from the human body in an efficient and relatively non-traumatic manner. The invention is applicable to fluid collections located within the thoracic, abdominal, or pelvic cavities, or within organs of the human body.

2. Discussion of the Related Art

A drainage catheter is generally a flexible tube with multiple side openings near the distal end, and is widely recognized as an efficient and effective device for removing fluid collections from the human body. Conventional procedures for placing the drainage catheter inside the human body are time-consuming and require the assistance of other devices including a puncture needle, guide wire, and dilator sheath. The puncture needle consists of an outer cannula having an elongated tube and an inner trocar with a sharpened tip projecting through the distal tip of the cannula.

In use, the puncture needle is first punctured into the human body to reach the fluid collection. The trocar needle is then removed. A specimen of the fluid is obtained by aspiration through the cannula so that the fluid nature of the collection can be confirmed before the actual drainage procedure. This collection is typically obtained before such specimen has been contaminated by an operating instrument.

A guide wire is then positioned to reach the fluid collection through the cannula. Once the guide wire is property positioned, the cannula is removed. A number of dilator sheaths with tapered distal tip ends, one at a time, are then inserted over the guide wire to dilate the stricture until the size of the drainage catheter is reached. The drainage catheter is then inserted over the guide wire to reach the fluid collection.

Once the drainage catheter is properly positioned, the drainage catheter is fixed externally onto the skin with a fixation device. Abnormal fluid can be removed by suction or drained or siphoned through the drainage catheter into a collection bag.

One disadvantage of this conventional method is that it involves redundant steps of inserting the guide wire and dilator sheaths to dilate the stricture, which can be eliminated by an assembled device specially designed for the drainage of the fluid collections from the human body.

A one-step drainage catheter has been designed to simplify the above procedure. The one-step drainage catheter is a device which includes a trocar preloaded within the catheter. The trocar has a sharp distal tip that protrudes out of the catheter. The trocar and the catheter are locked together at the hub, at the proximal end, so that they function as a unit.

When the one-step drainage catheter is in use, the combined unit of the trocar and catheter is inserted into the collection cavity. The trocar is then disengaged from the catheter and removed. The catheter remains with its distal end positioned for draining the fluid collection.

Although the one-step drainage catheter has greatly simplified the conventional procedure, there are two main disadvantages. First, forceful advancement of the combined unit of the trocar and catheter is required to bring the unit into the human body and to overcome the friction between the body tissue and the catheter tip. The catheter tip is positioned slightly behind the trocar tip, creating an abutment surface on the catheter tip against the body tissue. The abutment surface on the catheter tip is subject to substantial pressure during insertion into the body tissue, which causes great trauma for the patient.

Second, no fluid specimen can be obtained by simply applying the one-step drainage catheter, which is a crucial step to ensure that the catheter tip is properly positioned and the abnormal fluid drained. In some circumstances, the one-step drainage catheter is improperly positioned and no fluid can be drained after insertion. The one-step drainage catheter has to be reinserted and the patient has to suffer another puncture.

It is also helpful to extract the fluid specimen when the fluid collection is still uncontaminated by any instruments or device. Without the cannula being part of the device, the lumen now being occupied by the trocar, the specimen fluid can only be obtained by a separate needle puncture before the use of the one-step drainage catheter. In that case, the patient will suffer two punctures during the procedure.

U.S. Pat. No. 5,205,830 discloses a catheter assembly comprising a catheter, a cannula, and a dilator. According to the '830 patent, the cannula and dilator are preloaded inside the catheter. An introducer needle (also known as a trocar) is first inserted into the cavity to be drained. A guide wire is then inserted into the introducer needle and the introducer needle is removed. The catheter assembly device is then inserted over the guide wire to reach the fluid collection.

One disadvantage of the '830 patent is that the catheter is inserted into the human body with the cannula, before the specimen fluid can be obtained. Such insertion will encounter more resistance from the body tissue because of the relatively larger diameter of the catheter. If the catheter assembly is not positioned at the desired body cavity location and does not reach the fluid collection, which can be discovered only after insertion of the catheter assembly, the catheter assembly has to be re-inserted and the patient will suffer another puncture. An alternative is to obtain the fluid specimen by a separate needle puncture before insertion of the catheter assembly as described above, but the patient is still forced to suffer two punctures.

Known guide wires are used to guide the insertion of the catheter to reach the drainage system within the organs. A disadvantage is that the guide wire has to be separately held in a relatively stable position during the insertion of the catheter.

SUMMARY OF THE INVENTION

An embodiment of the present invention provides an easy drainage catheter assembly which comprises a trocar, a cannula, a catheter, and a catheter stiffener for removing abnormal fluid collections from cavities, or within organs of the human body.

Another embodiment of the present invention provides an easy drainage catheter assembly which removes abnormal fluid collections from cavities or within organs of the human body in an effective, efficient, and comparatively non-traumatic manner.

Another embodiment of the present invention provides an easy drainage catheter assembly which includes means to obtain fluid specimen from the fluid collection before the actual drainage of fluid.

Yet another embodiment of the present invention provides an easy drainage catheter assembly of which the easy drainage catheter assembly is inserted into the human body by a two-step approach. The first step being the insertion of the trocar and the cannula together and the second step being the insertion of the catheter stiffener and the catheter together.

Still yet another embodiment of the present invention provides an easy drainage catheter assembly which encounters comparatively less resistance from the body tissue during the insertion of the trocar and the catheter.

Another embodiment of the present invention provides an easy drainage catheter assembly which minimizes the damage on the body tissue if the first puncture does not reach the desired location and another puncture is required.

Yet another embodiment of the present invention provides an easy drainage catheter assembly of which the trocar can detach from the easy drainage catheter assembly after the easy drainage catheter assembly has been inserted into human body.

Still yet another embodiment of the present invention provides an easy drainage catheter assembly which consists of a catheter stiffener located between the outer catheter and the inner cannula for enhancing and maintaining the stiffness of the flexible catheter lengthwise during the insertion of the easy drainage catheter assembly into the human body.

Another embodiment of the present invention provides an easy drainage catheter assembly which consists of a guide wire with a torque device which can be secured with the cannula as a unit, thus eliminating the need for the operator to separately hold the guide wire during the insertion of the catheter.

Another embodiment of the present invention provides an easy drainage catheter assembly of which the catheter and the catheter stiffener as a unit can advance over the cannula to be inserted into the human body.

Another embodiment of the present invention provides an easy drainage catheter assembly of which the catheter consists of a tapered distal tip to minimize the resistance and friction encountered at the tip of the catheter during the insertion into body tissue.

Another embodiment of the present invention provides an easy drainage catheter assembly of which the catheter stiffener can advance further into the fluid collection beyond the cannula in the body cavity.

Yet another embodiment of the present invention provides an easy drainage catheter assembly of which the catheter can advance further into the fluid collection beyond the cannula in the body cavity.

Still yet another embodiment of the present invention provides an easy drainage catheter assembly with connectors at the proximal end for locking the various components of the easy drainage catheter assembly into a set unit to be advanced together.

Another embodiment of the present invention provides an easy drainage catheter assembly with connectors of different numbers, shapes, or colors of gripper wings to assist the user to distinguish the components of the easy drainage catheter assembly.

Yet another embodiment of the present invention provides a simpler, safer, and faster method of placing drainage catheters into the human body for removing abnormal fluid collections from cavities or within organs of human body.

An alternative embodiment of the present invention provides a method for assembling an easy drainage catheter, which includes a trocar, a cannula, a catheter stiffener, and a catheter, for removing abnormal fluid collections from cavities or within organs of human body.

An alternative embodiment of the present invention provides a simpler, safer, and faster method of placement of an easy drainage catheter assembly into a human body for removing abnormal fluid collections from cavities or within organs of human body. As an example, such a method may include the following:

(a) inserting the trocar and the cannula of the pre-assembled easy drainage catheter assembly as one set unit into a human body to reach the fluid collection;

(b) detaching and slideably removing the trocar from the easy drainage catheter assembly;

(c) removing specimen fluid from the fluid collection through the cannula by aspiration;

(d) slideably inserting the catheter and the catheter stiffener along the cannula into a human body to reach the fluid collection;

(e) slideably further inserting the catheter into the fluid collection;

(f) detaching and slideably removing the catheter and the catheter stiffener from the easy drainage catheter assembly; and (g) fixing the catheter externally onto the skin of the human body.

BRIEF DESCRIPTION OF THE DRAWING

The above and other aspects, features, and advantages of the present invention will become more apparent upon consideration of the following description of preferred embodiments, taken in conjunction with the accompanying drawing figures, wherein.

DETAILED DESCRIPTION OF PREFERRED EMBODIMENTS

In the following detailed description, reference is made to the accompanying drawing figures which form a part hereof and which show by way of illustration specific embodiments of the invention. It is to be understood by those of ordinary skill in this technological field that other embodiments may be utilized, and structural, as well as procedural, changes may be made without departing from the scope of the present invention.

Figures 1A, 1B, 1C:
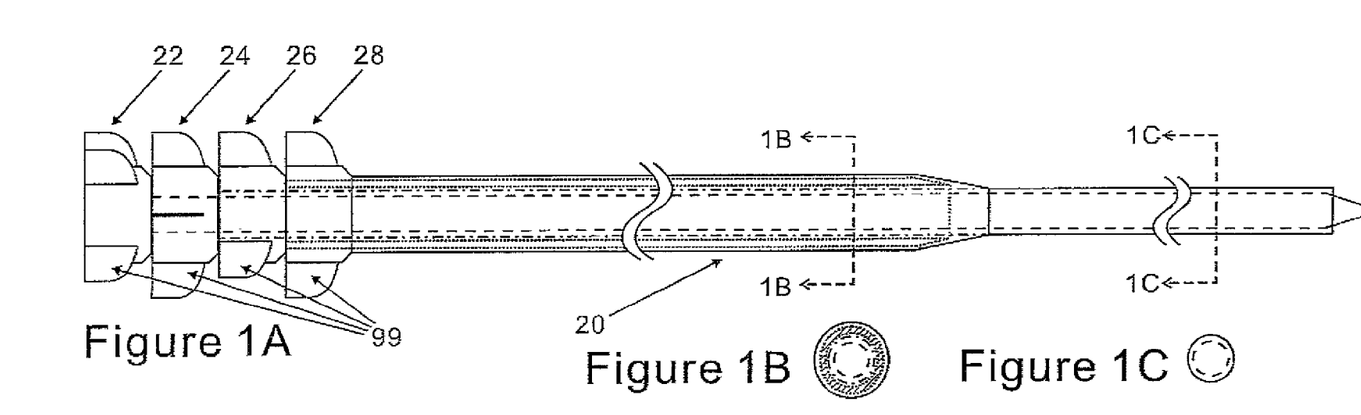
FIG. 1A is a side view of an easy drainage catheter assembly assembled in accordance with an embodiment of the present invention.
FIG. 1B is a cross-sectional view of the easy drainage catheter assembly of FIG. 1A, taken along line 1B-1B.
FIG. 1C is a cross-sectional view of the easy drainage catheter assembly of FIG. 1A, taken along line 1C-1C.

One embodiment of easy drainage catheter assembly 20 according to the present invention is illustrated in FIGS. 1A-1C. The easy drainage catheter assembly includes trocar 22, cannula 24, catheter stiffener 26, and catheter 28. Although described herein as a preferred device and method for removing fluid collections out of the human body, the embodiment may be utilized to perform other functions such as providing drainage to obstructed drainage systems in body organs such as, for example, the biliary system in the liver or urinary system in the kidney.

Figure 2:
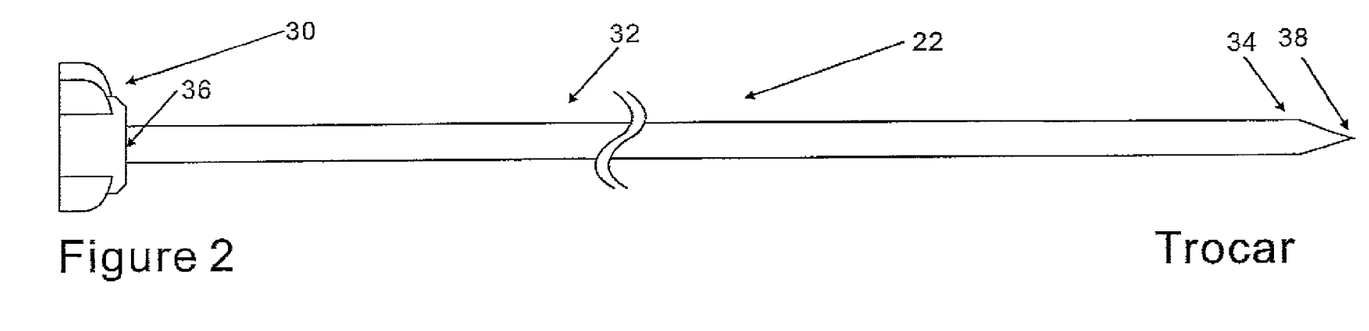
FIG. 2 is a side view of a trocar of the easy drainage catheter assembly in accordance with an embodiment of the present invention.

Various components of easy drainage catheter assembly 20 are described below in more detail, and further illustrated in FIGS. 2, 3, 4A, 4B, and 5A-5C. As shown in FIG. 2, trocar 22 includes proximal end 30, intermediate portion 32, and distal end 34. The proximal end is shown attached to conventional male Luer connector 36 for rotatably connecting with the proximal end of cannula 24. Distal end 34 forms a sharply pointed tip 38 for inserting through body tissue. The trocar may be formed from a sufficiently hard material such as steel, nitinol, metallic alloy, and the like.

By way of non-limiting example, trocar 22 has a diameter of approximately 1 mm, and a length of approximately 19 to 32 cm. However, the diameter and length may vary according to the site of the body cavity or organ inside the human body on which the easy drainage catheter assembly is to be applied.

Figure 3:
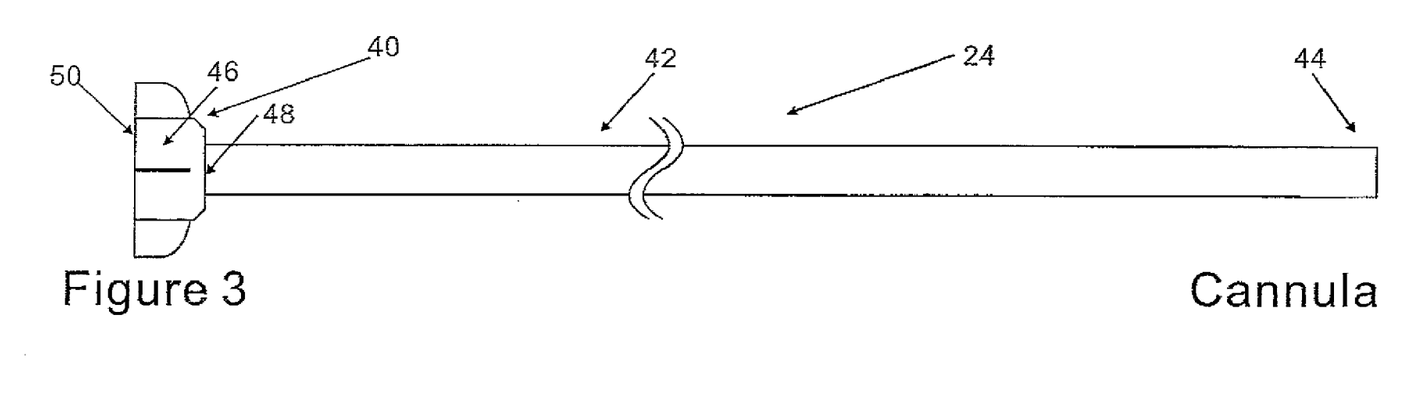
FIG. 3 is a side view of a cannula of the easy drainage catheter assembly in accordance with an embodiment of the present invention.

As shown in FIG. 3, cannula 24 includes proximal end 40, intermediate portion 42, and distal end 44. The proximal end is attached to conventional Luer connector 46, with male end 48 rotatably connecting with the proximal end of the catheter stiffener 26 and female end 50 receiving the male Luer connector 36 of trocar 22. The length of the cannula extending from proximal end 40 to distal end 44 is sized to receive intermediate portion 32 of the trocar 22 such that tip 38 of the trocar extends as shown in FIG. 1A, for instance, 1-3 mm beyond distal end 44 of the cannula 24. The central lumen (not shown) of the cannula is appropriately sized to slideably receive the trocar and is preferably about 1 mm in diameter, but may vary depending on the size of the trocar. As described further below, cannula 24 provides a mechanism for catheter stiffener 26 and catheter 28 to slideably insert over when entering into the human body, and also permits obtaining a fluid specimen from the fluid collection by aspiration. The cannula may be made of a hard material such as steel, nitinol, or metallic alloy, among others.

By way of non-limiting example, cannula 24 has a length of approximately 19-32 cm. However, the length of the cannula may vary according to the site of the body cavity or organ inside the human body on which the easy drainage catheter assembly is to be applied.

Figures 4A, 4B:
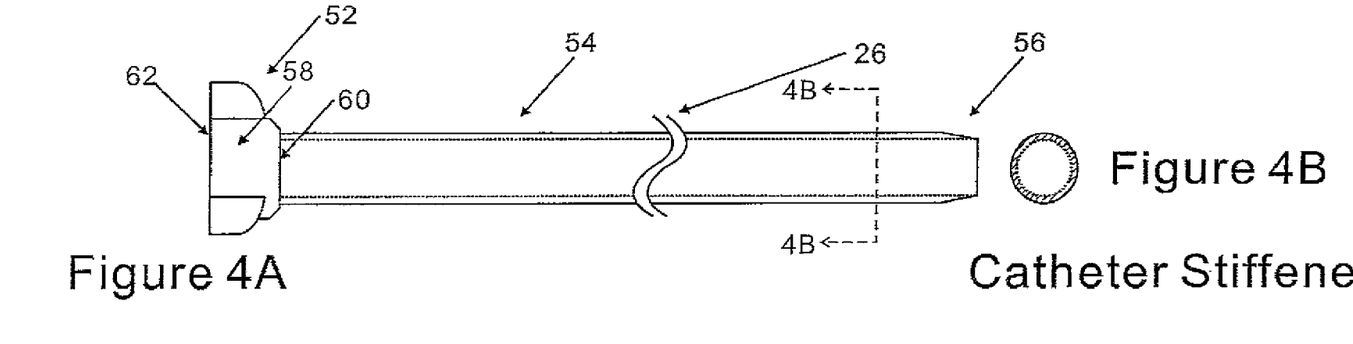
FIG. 4A is a side view of a catheter stiffener of the easy drainage catheter assembly in accordance with an embodiment of the present invention.
FIG. 4B is a cross-sectional view of the catheter stiffener of FIG. 4A, taken along line 4B-4B.

As shown in FIGS. 4A and 4B, catheter stiffener 26 includes proximal end 52, intermediate portion 54, and distal end 56. The proximal end is attached to a conventional Luer connector 58 with male end 60 rotatably connecting with the proximal end of catheter 28, and female end 62 receiving male end 48 of Luer connector 46 of cannula 24. Catheter stiffener 26 extends from proximal end 52 to distal end 56, and the outer diameter is sized to fill up the lumen of catheter 28, which will be further illustrated below. By way of non-limiting example, the outer diameter of the catheter stiffener is about 1.5-2.5 mm, but may vary depending on the size of the catheter.

The length of catheter stiffener 26 covers a proximal portion of cannula 24, and typically remains outside the human body when trocar 22 is inserted into the body cavity. The length of the distal portion of the cannula not covered by catheter stiffener 26 varies, for instance, from 7-13 cm, depending on the site of the fluid collection. Distal end 56 of the catheter stiffener may be tapered to match with the tapered distal end of the catheter.

The central lumen (not shown) of catheter stiffener 26 is appropriately sized to slideably receive cannula 24 and includes a diameter of about 1.5 mm or less, but may vary with the size of the cannula. The catheter stiffener may be formed from a stiff material such as, for example, nylon, polyester, or silicon.

By way of non-limiting example, the catheter stiffener may have a length of approximately 13-19 cm. However, the length may vary according to the site of the body cavity or organ inside the human body on which the easy drainage catheter assembly is applied.

Figure 5A:
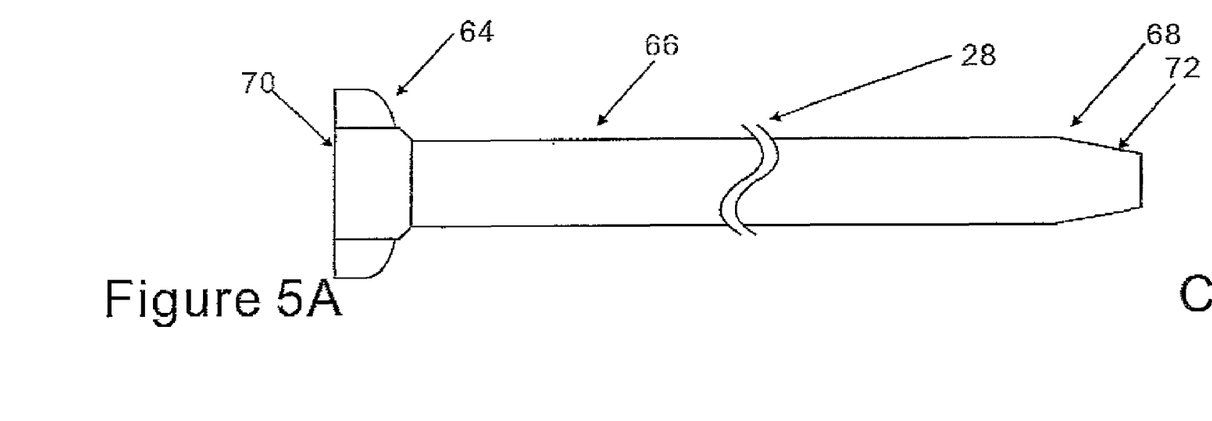
FIGS. 5A and 5B are side views of a catheter of the easy drainage catheter assembly in accordance with an embodiment of the present invention.
Figure 5B:
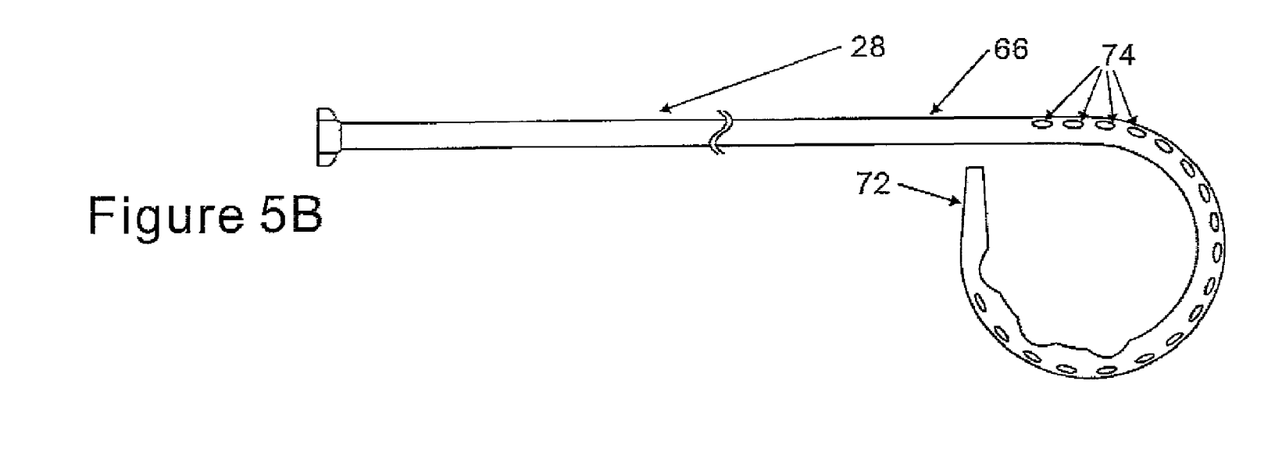

As shown in FIGS. 5A and 5B, catheter 28 includes proximal end 64, intermediate portion 66, and distal end 68. The proximal end is attached to a conventional female Luer connector 70 and receives male end 60 of Luer connector 58 of the catheter stiffener. Catheter 28 extends from proximal end 64 to distal end 68. The diameter of the central lumen (not shown) of the catheter is appropriately sized to slideably receive the catheter stiffener. Distal end 68 forms tapered tip 72, which reduces resistance encountered when entering body tissue, thereby making it easier to insert over the cannula into the body tissue.

A plurality of longitudinally spaced ports or openings 74 are formed in intermediate portion 66, proximal to tapered distal tip 72, and at axially spaced locations. Each opening directly communicates with the central lumen of the catheter for the drainage of fluid. Radiopaque markings may be formed along intermediate portion 66 at predetermined locations. These marking assist in fluoroscopically determining the positioning of the catheter.

Catheter 28 may be formed from soft pliable material such as polyurethane. To enhance and maintain the stiffness of intermediate portion 66 during insertion over cannula 24 into the human body, and to prevent the soft material of catheter 28 from bunching up, intermediate portion 54 of catheter stiffener 26 extends lengthwise to fill up the space between catheter 28 and cannula 24. Note that intermediate portion 54 of the catheter stiffener includes an outer diameter that is approximately sized to slideably insert into the central lumen of catheter 28. Stiffening catheter 28 eliminates the tendency of the soft material to bunch up, which would make it difficult for the catheter to be inserted into body tissue and cause trauma to the patient.

By way of non-limiting example, catheter 28 has a diameter of 2-4 mm, and a length of approximately 13-19 cm. However, the diameter may vary with the body cavity or organ to which the easy drainage catheter assembly is applied, and the length may vary according to the site of the body cavity or organ inside the human body.

FIG. 1A shows the pre-assembled easy drainage catheter assembly 20 ready for insertion as a unit. Trocar 22, cannula 24, catheter stiffener 26, and catheter 28 are coupled together by the Luer connectors located at the proximal end of the assembly.

Figure 6:
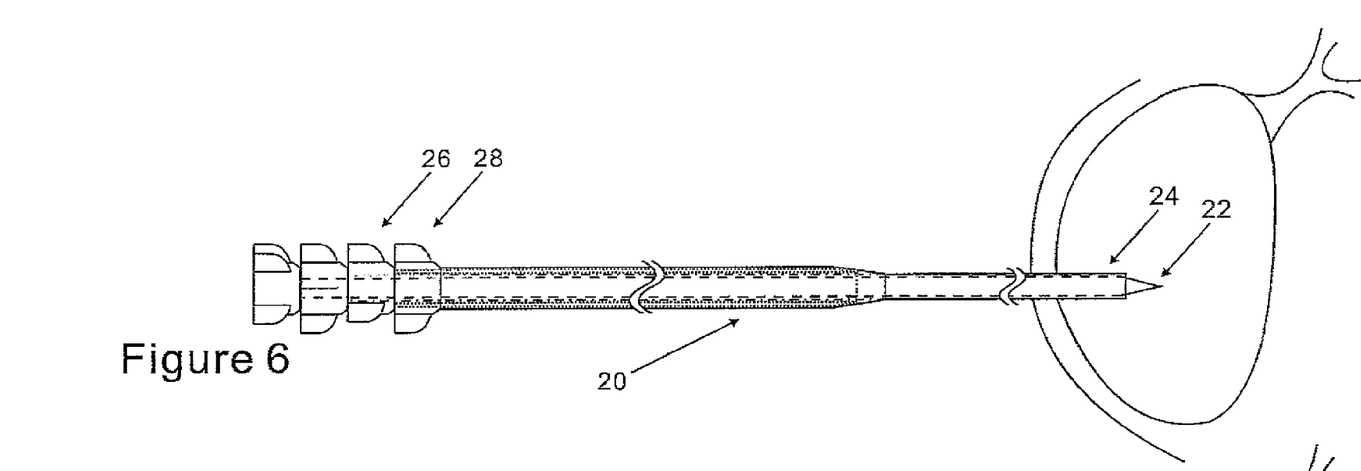
FIGS. 6, 7A-7C, and 8-10 illustrate use of the easy drainage catheter assembly in accordance with an embodiment of the present invention.

FIGS. 6, 7A-7C, and 8-10 illustrate a procedure using the easy drainage catheter assembly 20 to drain body fluid from a body cavity. As shown in FIG. 6, a first step is to insert the distal portion of trocar 22 and cannula 24 into the body cavity or the drainage system of the organ to be drained. Catheter stiffener 26 and catheter 28 remain outside the human body.

Figure 7A:
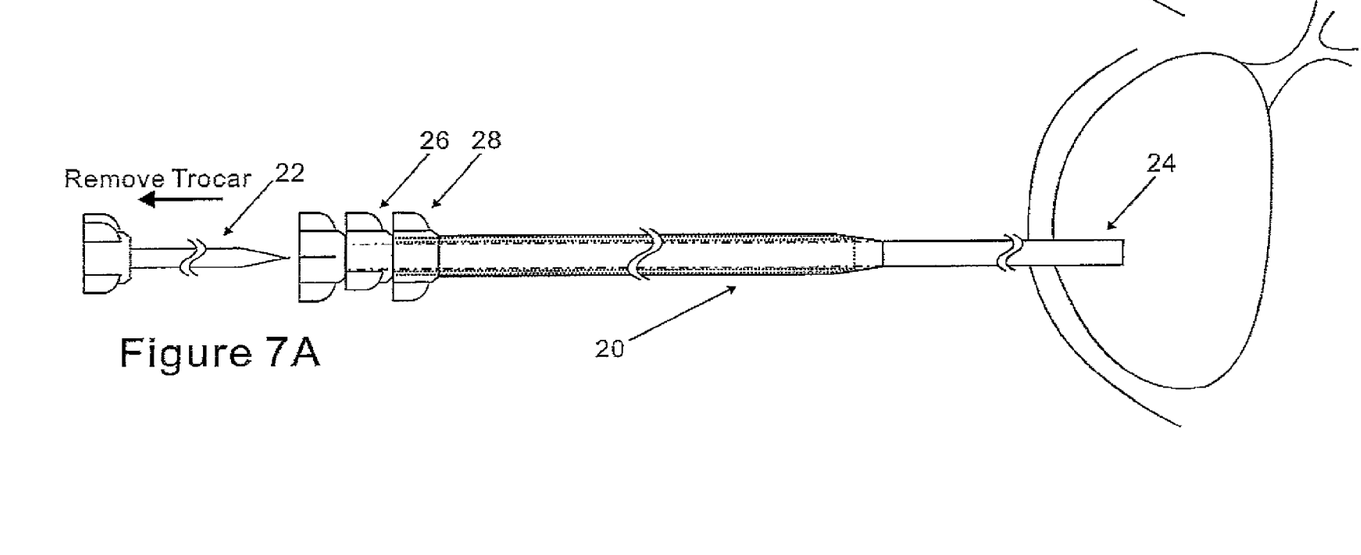

As shown in FIG. 7A, trocar 22 is then detached from cannula 24 by disengaging male Luer connector 36 of the trocar and female end 50 of Luer connector 46 of the cannula, and slideably retrieving trocar 22 out of the lumen of cannula 24. A specimen may then be obtained from the fluid collection in the body cavity by aspiration through the lumen of cannula 24. This step is to ensure that the cannula has been inserted into the desired location. Otherwise, the previous steps may be repeated. In that case, catheter stiffener 26 and catheter 28 have not yet been inserted into the body tissue, which saves the body tissue from being further torn apart by the catheter stiffener and the catheter of larger diameter.

Figure 7B:
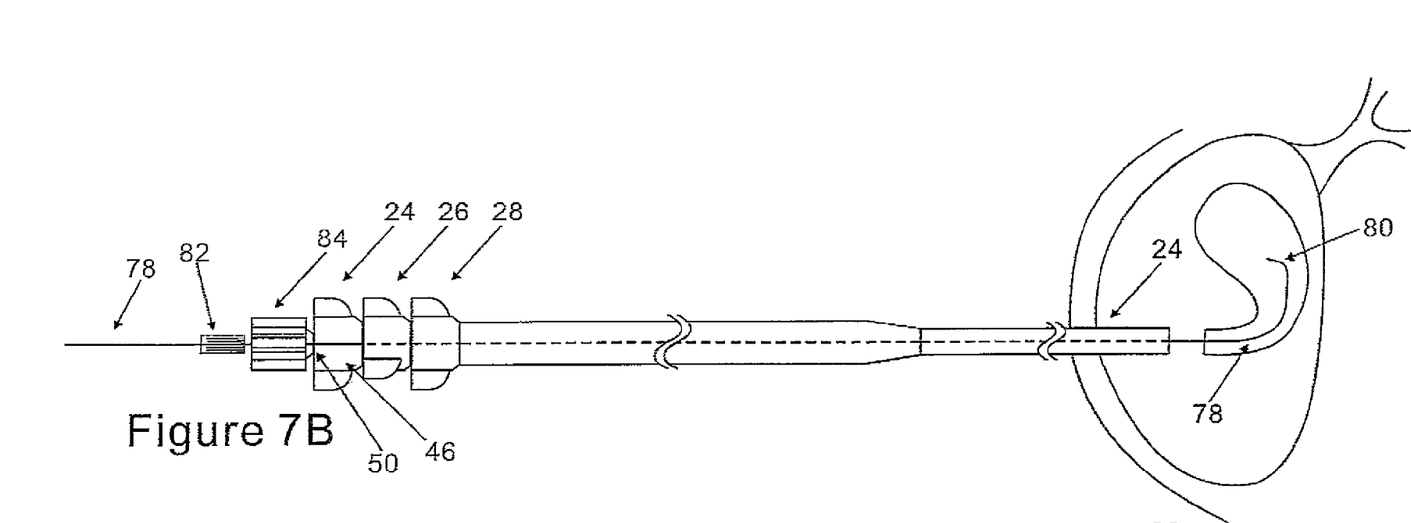

If fluid collection is within the organ, conventional guide wire 78 may be slideably inserted through the lumen of cannula 24 and into the drainage system within the organ, such as that shown in FIG. 7B. The guide wire often contains curved tip 80, which is useful for moving through curved regions of an organ duct.

Figure 7C:
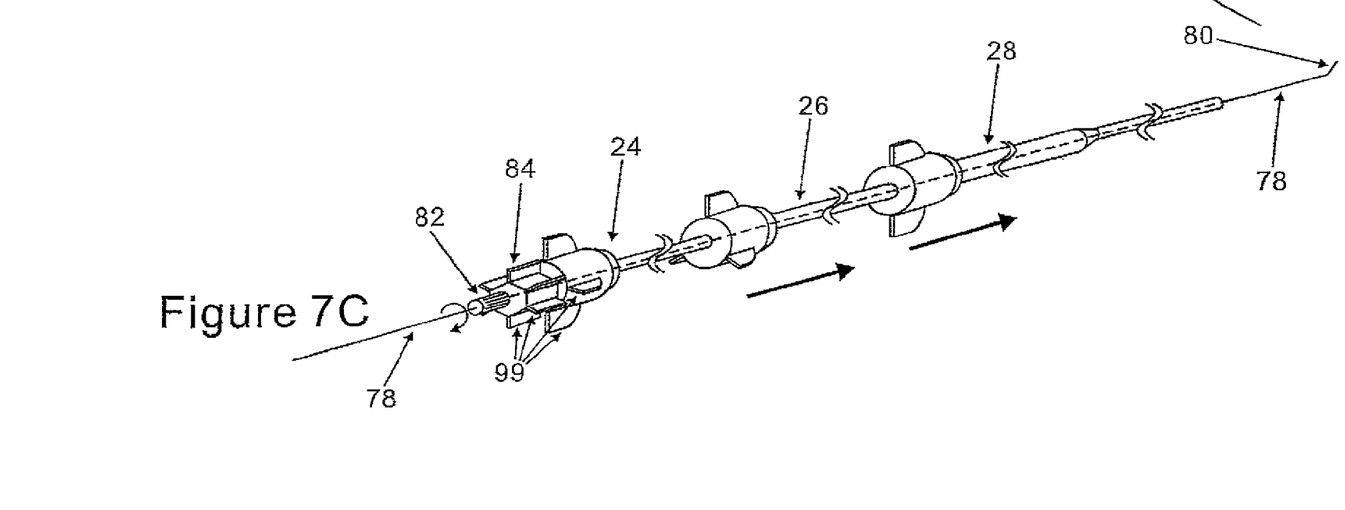

As shown in FIG. 7B, conventional torque device 82 is secured on guide wire 78, outside the human body. The torque device is useful for rotating the guide wire and turning curved tip 80, which enables the guide wire to enter the desired duct at cross sections of multiple ducts. Torque device 82 may be secured along guide wire 78 at a convenient position for the operator to control the guide wire. According to an embodiment, the torque device may include male Luer connector 84 for securing with female end 50 of Luer connector 46 of the cannula. As shown in FIG. 7C, the operator can therefore hold cannula 24 and guide wire 78 together in a stable position by holding one device. The operator is not required to handle these two devices separately during the insertion of catheter 28. Guide wire 78 acts as a guiding agent to facilitate the insertion of catheter 28, which will be described below.

Figure 8:
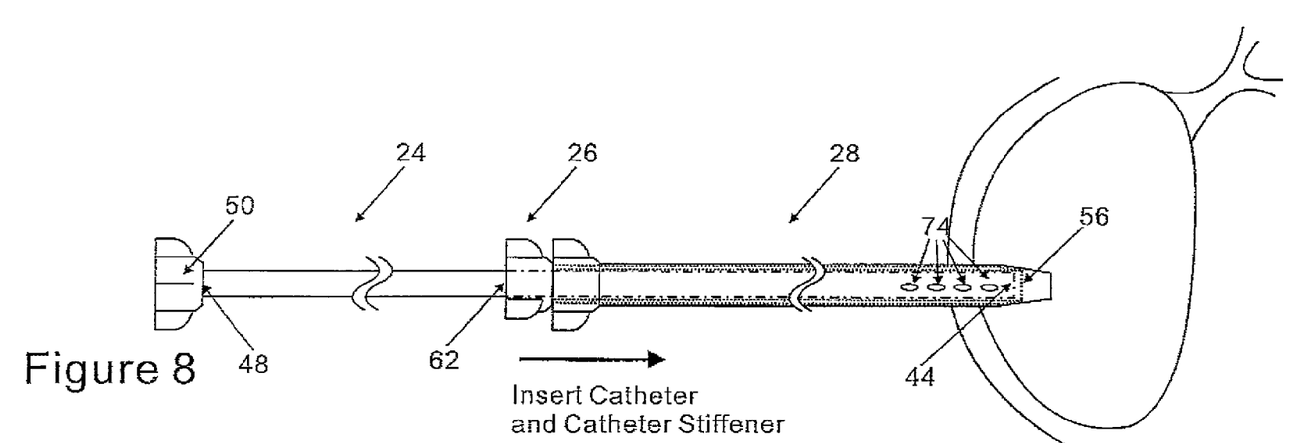

As shown in FIG. 8, female end 62 of the Luer connector of catheter stiffener 26 is then disengaged from male end 48 of the cannula. Catheter 28 and catheter stiffener 26 are then inserted as a unit into the body cavity over cannula 24. Distal end 56 of the catheter stiffener may extend distally beyond distal end 44 of the cannula to support catheter 28 if the catheter is to be further inserted to reach the fluid collection in the body cavity. As catheter stiffener 26 is made of a relatively stiff material, it typically does not extend more than 0.5 mm from cannula distal end 44. The catheter stiffener may be covered with an extended length of catheter 28, when it is advanced within the body, to prevent the catheter stiffener from accidentally damaging the soft tissue of the body cavity.

Figure 9:
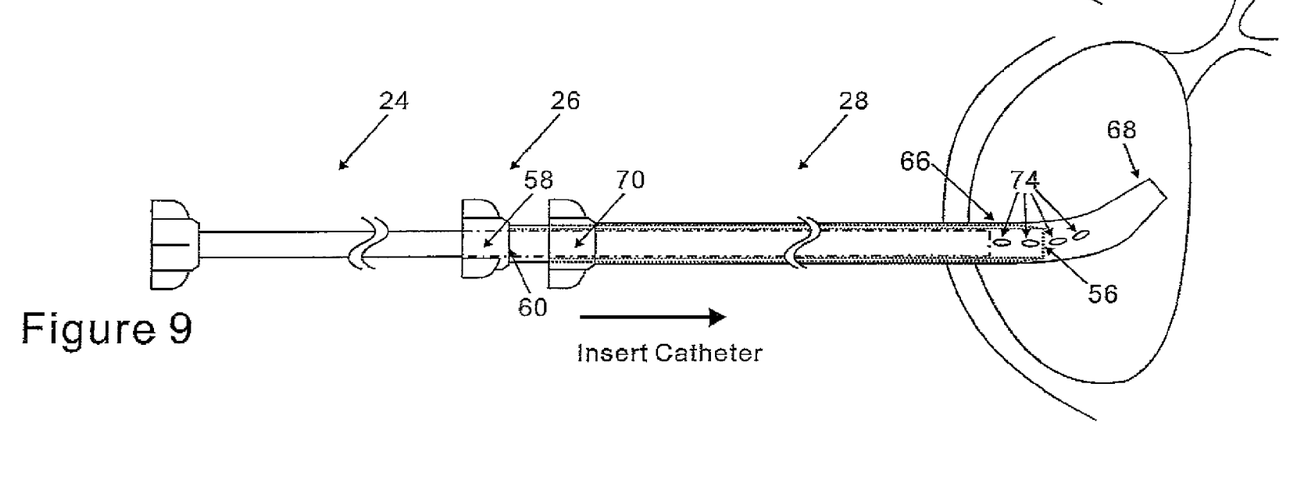

As shown in FIGS. 7C and 9, female Luer connector 70 of the catheter is disengaged from male end 60 of the stiffener. Intermediate portion 66 of the catheter is inserted beyond distal end 56 of catheter stiffener 26 to reach into the fluid collection, thus permitting openings 74 to contact the fluid collection.

If fluid collection is present within the organ, intermediate portion 66 may be further inserted over guide wire 78, and into the drainage system within the organ. As described above and shown in FIG. 7C, the locking of guide wire 78 and cannula 24 by torque device 82 frees the operator from holding the guide wire during the insertion of the catheter. The operator holds the cannula in a stable position and controls the insertion of the catheter, without separately holding the guide wire in place.

Figure 10:
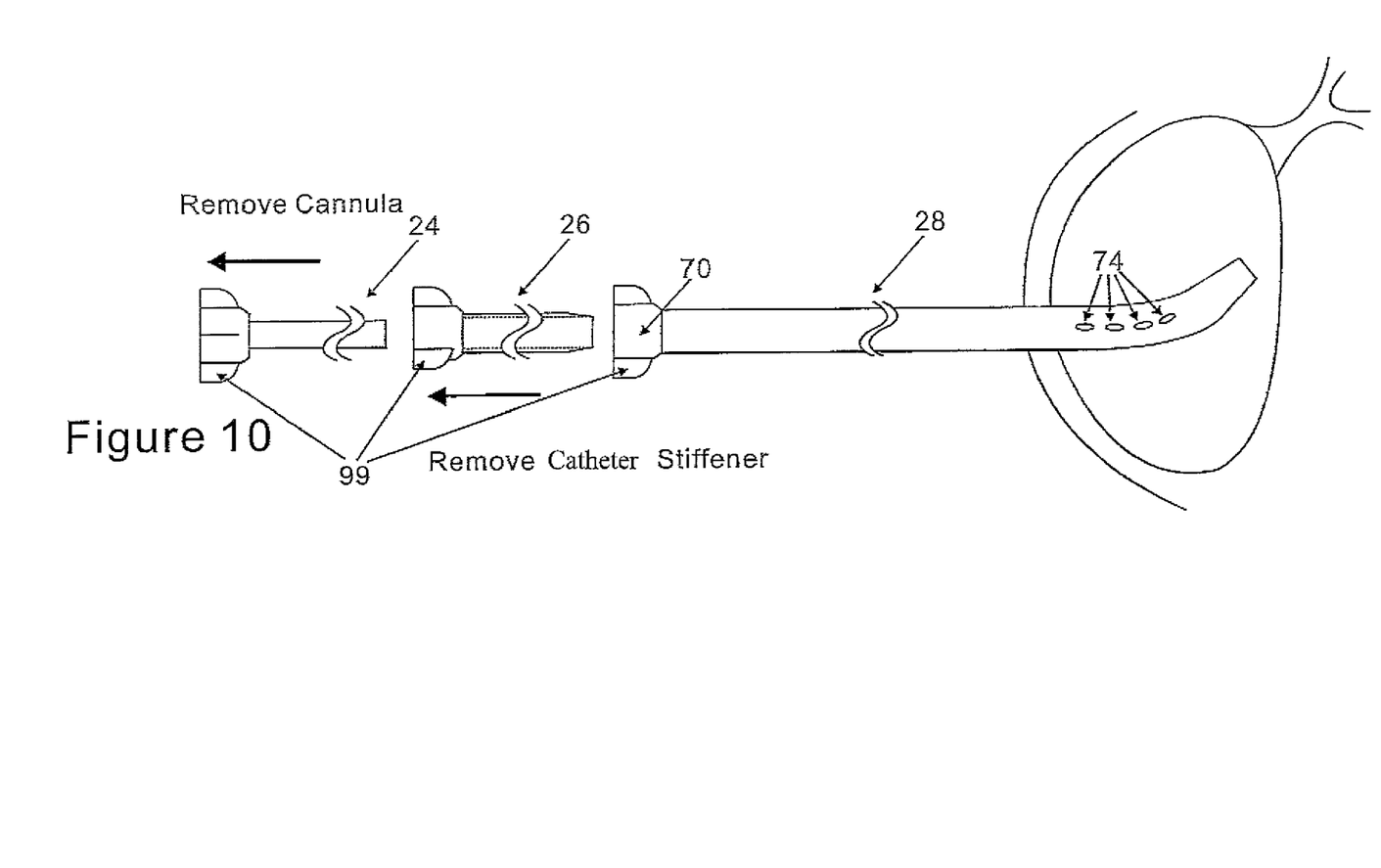

As shown in FIG. 10, cannula 24, guide wire 78 if used, and catheter stiffener 26 are slideably retrieved from catheter 28. Intermediate portion 66 of the catheter is fixed externally onto the skin surface with a fixation device or stitches. Finally, female Luer connector 70 is connected to a suction device or a connection tube of a drainage bag for the drainage of the abnormal fluid.

As shown in FIG. 1A, each Luer connector may include gripper wings 99 to make it easier for the operator to connect or disconnect the Luer connectors from each other. Each Luer connector may have a different number, shape, or color of gripper wings so that the operator can distinguish the various components of the easy drainage catheter assembly. By way of non-limiting example, the female Luer connector of catheter 70 contains two gripper wings, the Luer connector of catheter stiffener 58 contains three gripper wings, the Luer connector of cannula 46 contains four gripper wings; the male Luer connector of trocar 36 contains five gripper wings, and torque device 82 contains six gripper wings.

The present invention provides a unique, simplified approach for placement of a drainage catheter. Time-consuming and redundant steps utilized in conventional procedures, such as the repeated insertion of dilator sheaths, are eliminated.

The insertion step of the trocar and cannula may be separated from the insertion step of the catheter so that the device will encounter less resistance when entering into the human body. The present invention also reduces the likelihood of mis-positioning the drainage catheter since the specimen of the fluid collection can be obtained before the actual drainage. Such step is taken without the catheter being inserted into the body tissue, which would further tear off the body tissue. This two-step approach therefore eliminates unnecessary insertion of the catheter when the trocar is found mis-positioned upon testing of the fluid specimen. The patient need not suffer trauma encountered when the catheter is unnecessarily inserted into the body tissue.

While the invention has been described in detail with reference to disclosed embodiments, various modifications within the scope of the invention will be apparent to those of ordinary skill in this technological field. It is to be appreciated that features described with respect to one embodiment typically may be applied to other embodiments. Therefore, the invention properly is to be construed only with reference to the claims.

The invention claimed is:

1. A method for delivering a catheter to a body cavity of a patient using a drainage catheter assembly, said method comprising:
   (a) providing a pre-assembled drainage catheter assembly by connecting a trocar, a cannula, a catheter stiffener, and a catheter; where in a pre-assembled state, a distal end of said catheter and a distal end of said catheter stiffener are configured to terminate proximally relative to a distal end of said cannula and a distal end of said trocar;
   (b) inserting said trocar and said cannula into a body cavity;
   (c) disconnecting and slideably removing said trocar from the drainage catheter assembly and out of the body cavity;
   (d) disconnecting said catheter from said cannula and slideably inserting said catheter and said catheter stiffener as a set unit over said cannula and into the body cavity;
   (e) disconnecting said catheter from said catheter stiffener and slideably advancing said catheter into a fluid collection of the body cavity; and
   (f) slideably removing said cannula and said catheter stiffener from the drainage catheter assembly and out of the body cavity.

2. The method as recited in claim 1, wherein between (c) and (d), said method further comprises:
   collecting fluid from the fluid collection through said cannula.

3. The method as recited in claim 1, wherein between (e) and (f), said method further comprises:
   advancing said catheter stiffener through an end of said cannula.

4. The method as recited in claim 2, wherein between (e) and (f), said method further comprises:
   advancing said catheter stiffener through an end of said cannula.

5. A method for delivering a catheter into a drainage system within an organ of a patient using a drainage catheter assembly, said method comprising:
   (a) providing a pre-assembled drainage catheter assembly by connecting a trocar, a cannula, a catheter stiffener, and a catheter; where in a pre-assembled state, a distal end of said catheter and a distal end of said catheter stiffener are configured to terminate proximally relative to a distal end of said cannula and a distal end of said trocar;
   (b) inserting said trocar and said cannula into a human body;
   (c) disconnecting and slideably removing said trocar from the drainage catheter assembly and out of the human body;
   (d) inserting a guide wire into the drainage system through said cannula;
   (e) disconnecting said catheter from said cannula and slideably inserting said catheter and said catheter stiffener as a set unit over the cannula and into the human body;
   (f) disconnecting said catheter from said catheter stiffener and slideably advancing said catheter into the drainage system and over said guide wire;
   (g) slideably removing said cannula, said catheter stiffener, and said guide wire from the drainage catheter assembly and out of the human body.

6. The method as recited in claim 5, wherein between (c) and (d), said method further comprises:
   collecting fluid from the drainage system through said cannula.

7. The method as recited in claim 5, wherein between (d) and (e), said method further comprises:
   securing said guide wire with said cannula.

8. The method as recited in claim 6, wherein between (d) and (e), said method further comprises:
   securing said guide wire with said cannula.

\* \* \* \* \*